US00PP21490P2

(12) United States Plant Patent
Dümmen

(10) Patent No.: US PP21,490 P2
(45) Date of Patent: Nov. 16, 2010

(54) ***PELARGONIUM* PLANT NAMED 'DUEVICHER09'**

(50) Latin Name: *Pelargonium zonale*
Varietal Denomination: Duevicher09

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/586,393

(22) Filed: Sep. 21, 2009

(51) Int. Cl.
*A01H 5/00* (2006.01)

(52) U.S. Cl. ..... Plt./330
(58) Field of Classification Search ..... Plt./330

See application file for complete search history.

*Primary Examiner*—Annette H Para
(74) *Attorney, Agent, or Firm*—C. A. Whealy

(57) ABSTRACT

A new and distinct cultivar of Zonal *Geranium* plant named 'Duevicher09', characterized by its upright to outwardly spreading plant habit; vigorous growth habit; freely basal branching habit; dark green-colored leaves with a distinct zonation pattern; freely flowering habit; semi-double cherry red-colored flowers; and good garden performance.

1 Drawing Sheet

Botanical designation: *Pelargonium zonale.*
Cultivar denomination: 'Duevicher09'.

BACKGROUND OF THE INVENTION

The present invention relates to a new and distinct cultivar of Zonal *Geranium* plant, botanically known as *Pelargonium zonale*, and hereinafter referred to by the name 'Duevicher09'.

The new Zonal *Geranium* plant is a product of a planned breeding program conducted by the Inventor in Rheinberg, Germany. The objective of the breeding program is to create new vigorous Zonal *Geranium* plants with dark green-colored leaves and attractive flowers.

The new Zonal *Geranium* plant originated from a cross-pollination made by the Inventor in July, 2005 in Rheinberg, Germany of a proprietary selection of *Pelargonium zonale* identified as code number F-02-01, not patented, as the female, or seed, parent with a proprietary selection of *Pelargonium zonale* identified as code number Z98-2476-004, not patented, as the male, or pollen, parent. The new Zonal *Geranium* plant was discovered and selected by the Inventor as a single flowering plant from within the progeny of the stated cross-pollination in a controlled greenhouse environment in Rheinberg, Germany in May, 2008.

Asexual reproduction of the new Zonal *Geranium* plant by vegetative terminal cuttings in a controlled greenhouse environment in Rheinberg, Germany since May, 2008, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duevicher09'.

These characteristics in combination distinguish 'Duevicher09' as a new and distinct cultivar of Zonal *Geranium:*

1. Upright to outwardly spreading plant habit.
2. Vigorous growth habit.
3. Freely basal branching habit.
4. Dark green-colored leaves with a distinct zonation pattern.
5. Freely flowering habit.
6. Semi-double cherry red-colored flowers.
7. Good garden performance.

Plants of the new Zonal *Geranium* differ primarily from plants of the parent selections in flower color as plants of the female parent selection have purple-colored flowers and plants of the male parent selection have orange red-colored flowers.

Plants of the new Zonal *Geranium* can be compared to plants of *Pelargonium zonale* 'Duevicher', disclosed in U.S. Plant Pat. No. 14,079. In side-by-side comparisons conducted in Rheinberg, Germany, plants of the new Zonal *Geranium* differed from plants of 'Duevicher' in the following characteristics:

1. Plants of the new Zonal *Geranium* were more compact than plants of 'Duevicher'.
2. Plants of the new Zonal *Geranium* had larger leaves than plants of 'Duevicher'.
3. Plants of the new Zonal *Geranium* were more freely flowering than plants of 'Duevicher'.

BRIEF DESCRIPTION OF THE PHOTOGRAPH

The accompanying colored photograph illustrates the overall appearance of the new Zonal *Geranium* plant, showing the colors as true as it is reasonably possible to obtain in colored reproductions of this type. Colors in the photograph may differ slightly from the color values cited in the detailed botanical description which accurately describe the colors of the new Zonal *Geranium* plant. The photograph comprises a side perspective view of a typical flowering plant of 'Duevicher09' grown in a container.

DETAILED BOTANICAL DESCRIPTION

The aforementioned photograph and following observations and measurements describe plants grown in 10.5-cm containers in Rheinberg, Germany in a glass-covered greenhouse during the summer and under conditions which closely approximate commercial production. During the production of the plants, day and night temperatures averaged 18° C. and light levels averaged 4,500 lux. Plants were pinched one time three weeks after planting. Plants had been growing for 13 weeks when the photograph and the description were taken. In the detailed description, color references are made to The Royal Horticultural Society Colour Chart, 1995 Edition, except where general terms of ordinary dictionary significance are used.

Botanical classification: *Pelargonium zonale* 'Duevicher09'.

Parentage:

*Female, or seed, parent.*—Proprietary selection of *Pelargonium zonale* identified as code number F-02-01, not patented.

*Male or pollen parent.*—Proprietary selection of *Pelargonium zonale* identified as code number Z98-2476-004, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Upright to outwardly spreading plant habit; uniformly rounded; densely foliated.

*Growth and branching habit.*—Vigorous growth habit; freely basal branching habit with about three basal branches developing per plant; pinching enhances lateral branch development.

*Plant height to top of flower umbels.*—About 24 cm.

*Plant height to top of foliar plane.*—About 14 cm.

*Plant width.*—About 23 cm.

*Lateral branches.*—Length: About 6 cm. Diameter: About 6 mm. Internode length: About 1.7 cm. Texture: Pubescent. Strength: Moderately strong. Color: Close to 144A to 144B.

Foliage description:

*Arrangement.*—Alternate; simple.

*Length.*—About 6.3 cm.

*Width.*—About 7.9 cm.

*Shape,*—Reniform.

*Apex.*—Acute.

*Base.*—Cordate.

*Margin.*—Crenate.

*Venation pattern.*—Palmate.

*Texture, upper surface.*—Pubescent.

*Texture, lower surface.*—Smooth, glabrous.

*Color.*—Developing and fully expanded leaves, upper surface: Close to 137A; venation, close to 144A to 144B. Developing and fully expanded leaves, lower surface: Close to 137B to 137C; venation, close to 144A to 144B. Zonation pattern: Distinct. Distance from margin: About 7 mm. Width: About 1.2 cm. Color: Close to 147A.

*Petiole.*—Length: About 7.7 cm. Diameter: About 2.2 mm. Texture, upper and lower surfaces: Smooth, glabrous. Color, upper surface: Close to 144A. Color, lower surface: Close to 143A.

Flower description:

*Flower arrangement.*—Semi-double rotate flowers arranged in rounded hemispherical umbels arising from apical leaf axils; umbels displayed above the foliage on moderately strong peduncles; flowers face upright to outward.

*Fragrance.*—Not detected.

*Quantity of flowers.*—Freely flowering habit; about 27 flowers and flower buds per umbel.

*Flowering season.*—Year-round under greenhouse conditions; in outdoor nurseries and gardens in Germany flowering is continuous from spring throughout the summer; plants begin flowering about eight weeks after planting.

*Flower longevity.*—Individual flowers last about five to seven days on the plant; flowers persistent.

*Umbel height.*—About 5.2 cm.

*Umbel diameter.*—About 7 cm.

*Flower diameter: About* 5 cm.

*Flower depth* (*height*).—About 2.5 cm.

*Flower buds.*—Length: About 1.2 cm. Diameter: About 6.3 mm. Shape: Ovoid. Color: Close to 74B to 74C and 144A.

*Petals.*—Quantity per flower: About five. Length: About 2.6 cm. Width: About 2.2 cm. Shape: Obovate. Apex: Rounded. Base: Attenuate. Margin: Sinuate. Texture, upper and lower surfaces: Smooth, glabrous. Color: When opening, upper surface: Close to 45A and 57A. When opening, lower surface: Close to 46C. Fully opened, upper surface: Close to 45B and 57A; color becoming closer to 46A with development. Fully opened, lower surface: Close to 43A; color becoming closer to 46A to 46B with development.

*Petaloids.*—Quantity per flower: About three. Length: About 2.1 cm. Width: About 1.1 cm. Shape: Obovate. Apex: Rounded. Base: Attenuate. Margin: Sinuate. Texture, upper and lower surfaces: Smooth, glabrous. Color: When opening and fully opened, upper surface: Close to 45A and 57A. When opening and fully opened, lower surface: Close to 46C.

*Sepals.*—Quantity per flower: Five, arranged in a single whorl. Length: About 1.1 cm. Width: About 3.7 mm. Shape: Ensiform. Apex: Apiculate. Base: Acute. Margin: Entire. Texture, upper and lower surfaces: Smooth, glabrous. Color, upper surface: Close to 144A tinted with close to 45D. Color, lower surface: Close to 144A tinted with close to 46A.

*Peduncle* (*umbel stem*).—Length: About 12.3 cm. Diameter: About 3.7 mm. Strength: Moderately strong. Texture: Smooth, glabrous. Color: Close to 144A.

*Pedicel* (*individual flower stem*).—Length: About 2.5 cm. Diameter: About 1.5 mm. Strength: Moderately strong. Texture: Smooth, glabrous. Color: Close to 144A tinted with close to 187A.

*Reproductive organs.*—Androecium: Stamen quantity per flower: About five. Filament length: About 7.3 mm. Filament color: Close to 155C and 63C. Anther length: About 2 mm. Anther shape: Oval. Anther color: Close to 61A to 61B. Pollen amount: Moderate.

Pollen color: Close to 28A. Gynoecium: Pistil quantity per flower: One. Pistil length: About 9 mm. Stigma shape: Parted. Stigma color: Close to 45A to 46A. Style length: About 2 mm. Style color: Close to 46A. Ovary color: Close to 144A.

*Seed/fruit.*—Seed and fruit development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 5° C. to about 40° C. and have demonstrated good garden performance.

It is claimed:

1. A new and distinct Zonal *Geranium* plant named 'Duevicher09' as illustrated and described.

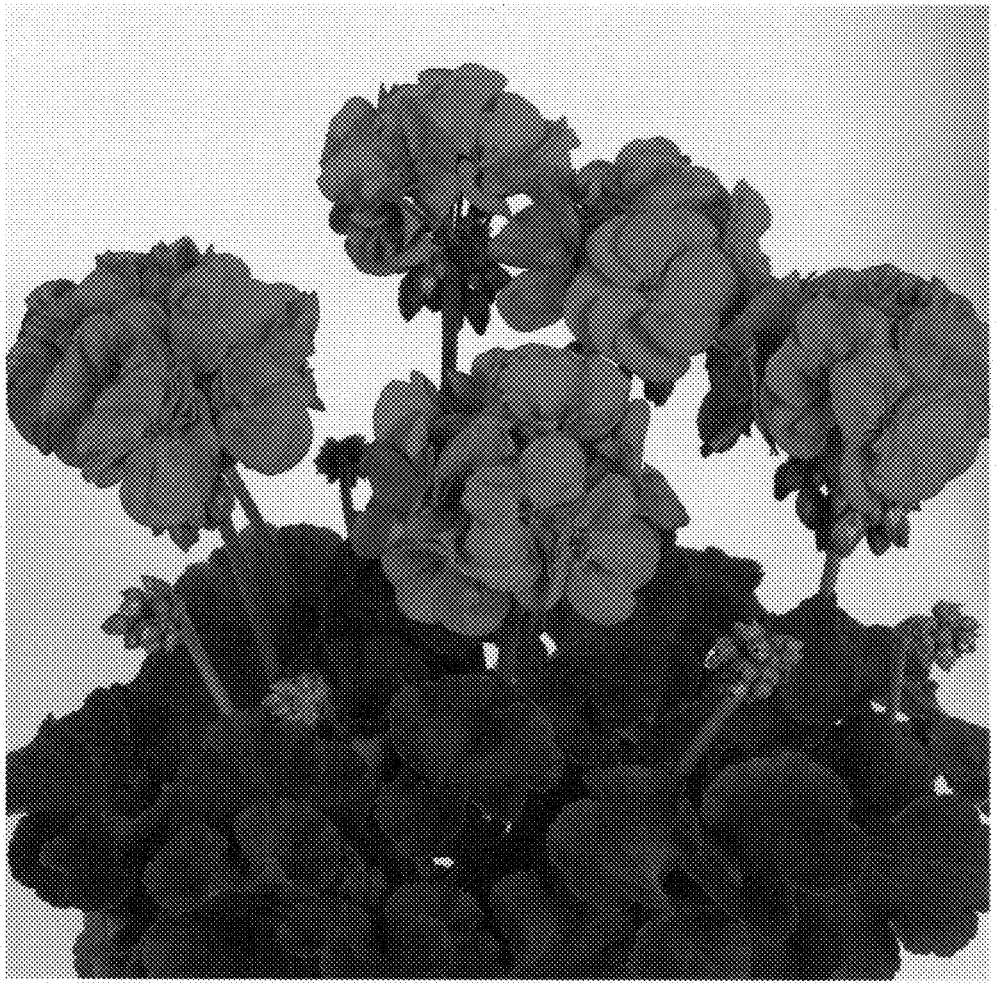

* * * * *